Figure 1:
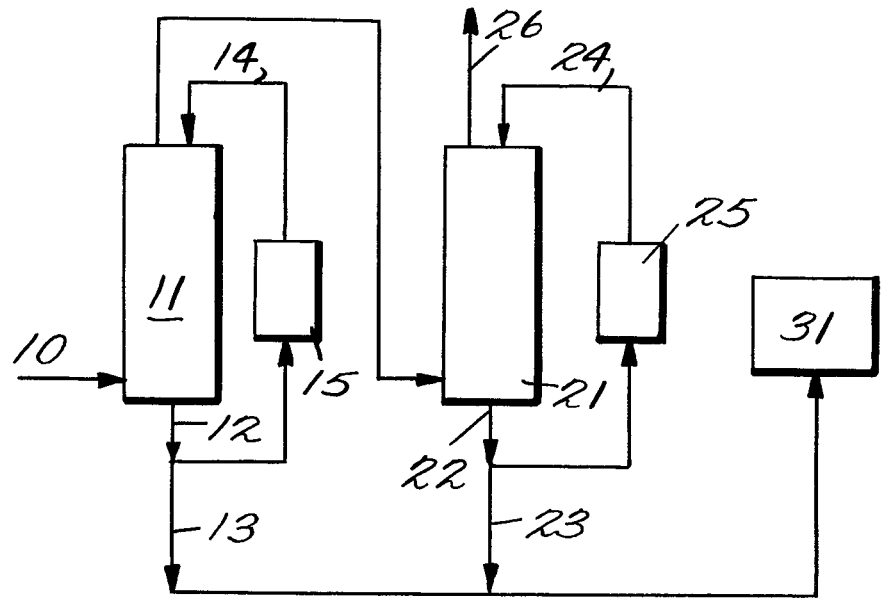

United States Patent [19]

Beschke et al.

[11] 4,237,299
[45] Dec. 2, 1980

[54] PROCESS FOR THE RECOVERY OF PYRIDINE AND 3-METHYLPYRIDINE

[75] Inventors: Helmut Beschke, Hanau; Franz-Ludwig Dahm, Alzenau; Heinz Friedrich; Gerd Schreyer, both of Hanau, all of Fed. Rep. of Germany

[73] Assignee: Deutsche Gold- und Silber-Scheideanstalt vormals Roessler, Frankfurt am Main, Fed. Rep. of Germany

[21] Appl. No.: 748,041

[22] Filed: Dec. 6, 1976

[30] Foreign Application Priority Data

Dec. 6, 1975 [DE] Fed. Rep. of Germany ....... 2554946

[51] Int. Cl.³ ............................................ C07D 213/12
[52] U.S. Cl. ..................................... 546/250; 546/251
[58] Field of Search .................... 260/290 P; 546/250, 546/251

[56] References Cited

U.S. PATENT DOCUMENTS 4,171,445   10/1979   Beschke et al. .................. 546/250

Primary Examiner—Alan L. Rotman
Attorney, Agent, or Firm—Cushman, Darby & Cushman

[57] ABSTRACT

Pyridine and 3-methylpyridine prepared by the catalytic reaction of acrolein or a mixture of acetaldehyde and acrolein with ammonia is recovered from the gas mixture formed by cooling the gas mixture and working up the condensate separated in the cooling. The gaseous mixture is first cooled to a temperature between 40° and about 80° C. and then cooled to a temperature between about 10° and below 40° C.

10 Claims, 2 Drawing Figures

PROCESS FOR THE RECOVERY OF PYRIDINE AND 3-METHYLPYRIDINE

The invention is directed to a process for the recovery of pyridine and 3-methlpyridine from the gas mixture formed in the catalytic reaction of acrolein or a mixture of acetaldehyde and acrolein with ammonia.

There are numerous processes for the production of pyridine and 3-methylpyridine by catalytic reaction of acrolein or acetaldehyde and acrolein with ammonia in the gas phase. These processes differ essentially in the catalysts used. There are especially added catalysts which are prepared by treating with oxygen at temperatures of 550° to 1200° C. compounds of the elements Al, F and O which compounds also contain at least one element of the second, third or fourth groups of the periodic system (German Offenlegungsschrift No. 2,151,417 and related Beschke U.S. Pat. No. 3,898,177) or at least two elements of the second, fourth, fifth or sixth groups of the periodic system (German Offenlegungsschrift No. 2,224,160 and related Beschke U.S. Pat. No. 3,960,766) or at least one element of the second main group of the periodic system (German Offenlegungsschrift No. 2,239,801 and related Beschke U.S. Pat. No. 3,917,542). The catalysts are used in fixed bed or in fluidized bed. The reaction generally is carried out at temperatures between 300° and 500° C., advantageously in the presence of inert gases, as for example nitrogen and with the use of excess ammonia. The entire disclosures of Beschke Pat. Nos. 3,898,177; 3,917,542 and 3,960,766 are hereby incorporated by reference and relied upon.

The gas mixture formed in the catalytic reaction contains pyridine, 3-methylpyridine and, in a given case, unreacted aldehydes, ammonia and byproducts such as other substituted pyridines and pyridine derivatives, quinoline and isoquinoline derivatives, isobutyronitrile, propionitrile, methane and ethylene. The working up of the gaseous mixture is essentially directed to the recovery of pyridine and 3-methylpyridine and to the recovery of excess ammonia. For example, the reaction mixture is cooled to 0° C., the condensate separating extracted with benzene and the pyridine recovered from the extract of the mixture by distillation (*Chem. Techn.*, Vol. 22, 1970, pages 745–748). Or the reaction mixture is washed with water, the wash liquid extracted by methylene chloride, for example, and the extract fractionally distilled to recover the pyridine (German OS No. 2,239,801 and Beschke U.S. Pat. No. 3,917,542).

To the extent it remains in the residual gas, the ammonia can be returned with this into the catalysis stage. To be sure in the known process a considerable portion, using a gas wash with water even a more substantial part, of the ammonia is separated from the gaseous mixture with the reaction products. Then it requires a recovery of the ammonia by separation of the reaction product.

There has been found a process for the recovery of pyridine and 3-methylpyridine from the gaseous mixture resulting from the catalytic reaction of acrolein or acetaldehyde and acrolein with ammonia by cooling the gaseous mixture and working up the separating condensate found in the cooling, which process comprises first cooling the gaseous mixture to a temperature between 40° and about 80° C. and then cooling further to temperatures between about 10° and below 40° C.

By means of this step-wise cooling of the gaseous mixture in a simple way the reaction products, namely the pyridine and 3-methylpyridine, are separated from the residual gas, especially from the excess, unreacted ammonia. The reaction product is thereby very substantially separated off while the ammonia remains almost completely in the residual gas. The necessary special separation of the ammonia from the reaction products of the known processes consequently is saved. The excess ammonia is available directly for reuse in the catalytic reaction. The volume of the separating condensate containing reaction product is substantially smaller than in the known process, the working up consequently is simpler. The pyridine and 3-methylpyridine is recovered with better yields than in the known processes.

According to the process of the invention there can be recovered pyridine and 3-methylpyridine from all gaseous mixtures which are formed in the customary processes of catalytic reaction of acrolein or a mixture of acetaldehyde and acrolein with ammonia in the gas phase. The warm gases are cooled directly in a first step to temperatures between 40° and about 80° C., preferably to temperatures between 40° and 60° C., and in a second step to temperatures between about 10° and below 40° C., preferably to temperatures between 20° and below 40° C.* The pressure can be chosen substantially at pleasure, however, it is recommended in order to use a simple apparatus to operate at normal pressure or only slightly lower or elevated pressure. Slightly deviating pressures from normal pressure occur in a given case because the gases are pressed or sucked through the equipment.

* Preferably the cooling in the second step is to a temperature at least 20° C. below the temperature of cooling in the first cooling step.

For carrying out the process of the invention there can be used customary apparatus suitable for the cooling of gases, for example, pipe bundle condensers, coil condensers or especially gas washers. As gas washers there can be used for example wash columns or spray washers or jet washers in combination with wash columns.

Figure 2:
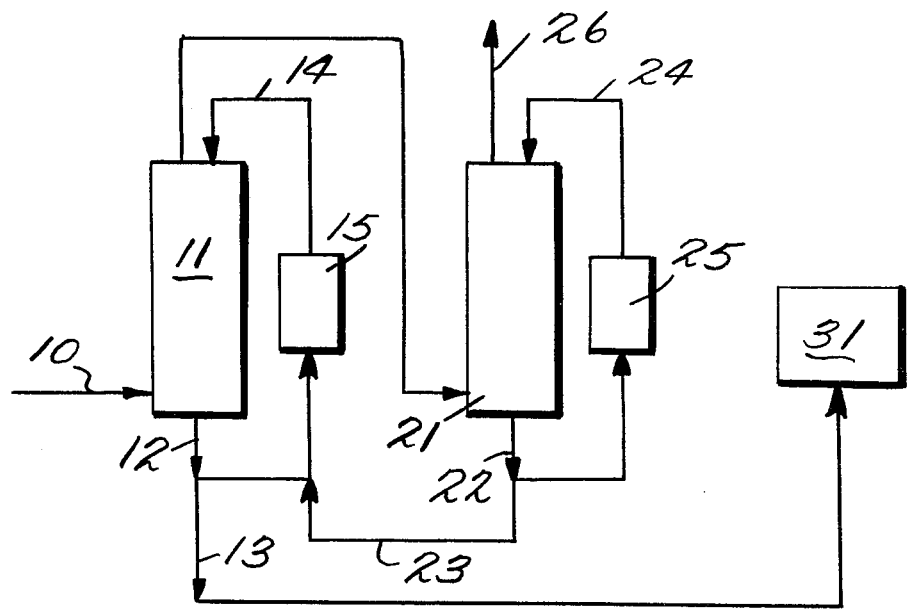

The invention will be understood best in connection with the drawings wherein:

FIG. 1 is a schematic illustration of one apparatus for carrying out the process of the invention; and, FIG. 2 is a schematic illustration of a modified apparatus for carrying out the process of the invention.

In the case of employing gas washers it is advantageous to use the condensate produced as cooling liquid for cooling the gases. For this purpose there is suitably used an arrangement according to FIG. 1. The warm gases 10 are led for the cooling in the first step into a gas washer 11. The condensate 12 containing the reaction products pyridine and 3-methylpyridine flowing out of this washer is led only in part, preferably a small part, via line 13 to further working up 31 while the other, preferably greater part 14 is cooled in a heat exchanger 15 and then returned as cooling liquid into the gas washer. The gases leaving the gas washer 11 are led into another gas washer 21 for the cooling in the second step. Also in this step the condensate 22 flowing out is only led in part, preferably a small part 23 to the further working up 31, the other, preferably greater, part 24, however, after cooling in a heat exchanger 25 is led back into the gas washer 21 as cooling liquid. Which part of the condensate 12 or 22 is led back as cooling liquid 14 or 24 depends on the particular process, generally chiefly according to the type of washer, amount, composition and temperature of the supplied gases, as well as according to the temperature of the cooling liquid and the temperature to which the gases should be cooled. The residual gas 26 which is very substantially free of the reaction product, is advantageously returned to the catalytic reaction and again added.

An especially advantageous procedure is shown in FIG. 2. This differs from FIG. 1 in that the partial stream 23 is not led to the further working up 31, but instead is led via the heat exchanger 15 into the gas washer 11 of step 1.

The condensate containing the reaction products separating upon cooling the gases according to the invention generally consists of an aqueous and a non-aqueous liquid phase. The working up of the condensate and the recovery of pyridine and 3-methylpyridine from the condensate can take place in the same manner as known processes, for example, by an extraction and subsequent distillation of the extract, e.g., as shown in Beschke U.S. Pat. No. 3,917,542, Example 1 or Beschke U.S. Pat. No. 3,898,177, Example 1, Beschke U.S. Pat. No. 3,960,766, Example 1(a).

For this purpose the condensate is treated with an extractant. Chiefly there are employed organic liquids whose boiling points are not above 95° C., which have only slight miscibility with water but form an azeotropic mixture with water having a boiling point below 95° C. and besides will take up pyridine and 3-methylpyridine. For example, there are suitable cyclohexanes, chlorinated alkanes, e.g., methylene chloride and carbon tetrachloride. Especially advantageous is the use of benzene. It is advantageous to use per part by volume of condensate 0.2 to 1.0 parts by volume, preferably 0.3 to 0.7 parts by volume of extractant. The aqueous phase remaining in the extraction contains insignificant amount of ammonia and, in a given case, unreacted aldehyde as well as small amounts of other organic materials. Generally it can be discarded. The fractional distillation for the recovery of pure pyridine and 3-methylpyridine from the extract is suitably carried out at normal pressure.

The process of the invention is especially suitable for recovery of pyridine and 3-methylpyridine from reaction gases produced in the reaction employing the catalysts of German OS No. 2,151,417 and related Beschke U.S. Pat. No. 3,898,177, German OS No. 2,224,160 and related U.S. Pat. No. 3,960,766, German OS No. 2,239,801 and related Beschke U.S. Pat. No. 3,917,542, and in a given case using the process of German OS No. 2,449,340 and related Beschke U.S. application Ser. No. 622,488, filed Oct. 15, 1975. The entire disclosure of this Beschke U.S. application is hereby incorporated by reference and relied upon.

Beschke U.S. Pat. No. 3,898,177 describes the catalyst in claim 1 as consisting essentially of oxygen containing compounds of Al, F, at least one of the elements B and Si and at least one element from the second and fourth groups of the periodic system selected from the group consisting of Mg, Ba, Zn, Sn and Zr, said catalyst having been prepared by heating in the presence of oxygen at a temperature of 600° to 800° C.;
1. aluminum, aluminum oxide or an aluminum compound convertible to the oxide at said temperature,
2. a compound of fluorine, said fluorine having been added as ammonium fluoride, ammonium hydrogen fluoride, hydrogen fluoride, fluoboric acid, fluosilicic acid, boron trifluoride, magnesium fluoborate, magnesium fluosilicate, zinc fluosilicate or barium fluosilicate,
3. boron, silicon, boric oxide, silica or a compound of boron or silica convertible to the oxide at said temperature and
4. magnesium, zinc, tin, zirconium, magnesium oxide, zinc oxide, tin oxide or a compound of zirconium or barium convertible to the oxide at said temperature, the atomic ratio of Al to F being from 1000:25 to 1000:800 and the atomic ratio of Al to the total of (3) and (4) being from 1000:5 to 100:200, the atomic ratio of the total of boron and silicon to the other element from the second and fourth groups being between 1 to 10 and 10 to 1.

Beschke U.S. Pat. No. 3,917,542 in claim 1 describes the catalyst as having been prepared by heating at 600° to 800° C. In the presence of gaseous oxygen, (1) aluminum metal, aluminum oxide or a compound of aluminum convertible to the oxide upon heating with gaseous oxygen at 600° to 800° C., (2) ammonium fluoride, hydrogen fluoride or a fluoride of an element of the second main group of the periodic system and (3) at least one element of the second main group of the periodic system, the oxide of said element or a compound of said element convertible to the oxide in the presence of gaseous oxygen at a temperature of 600° to 800° C., said catalyst consisting essentially of the elements Al, F, O and the element of the second main group of the periodic system.

Beschke U.S. Pat. No. 3,960,766 in claim 1 describes the catalyst as consisting essentially of the product obtained by treating with oxygen at a temperature of 550° to 1200° C. compounds of the elements Al, F and O and at least two other elements selected from the second, fourth, fifth and sixth groups of the periodic system, said two other elements being selected from the group consisting of Mg, Ba, Zr, Sn, Ti, P, Ta, Sb and S, the ratios of the elements being Al to F of between 1000 to 10 and 1000 to 800 and of Al to the elements of the second, fourth, fifth and sixth groups being between 1000 to 5 and 1000 to 2000.

As stated, however, these three Beschke U.S. patents also disclose a pretreatment temperature range of 550° to 1200° C.

In forming the pyridine and 3-methylpyridine, acrolein (or acrolein and acetaldehyde) and ammonia are added in gaseous form as is customary. Usually for each mole of acrolein (or acrolein and acetaldehyde) there is used at least 1 mole of ammonia. Usually the acrolein (or acrolein and acetaldehyde) and ammonia are used in the molar ratio of from 1.0 to 1.0 up to 1.0 to 3.0, especially from 1.0 to 1.3 up to 1.0 to 2.5. Suitably there can be additionally introduced an inert gas, e.g., nitrogen. Advantageously there are used 0.5 to 3.0 moles of inert gas per mole of acrolein (or mixture of acrolein and acetaldehyde). Preferably 1.0 to 2.5 moles of insert gas are employed per mole of acrolein (or acrolein and acetaldehyde). Other inert gases include, for example, argon or helium.

The temperature as stated above is usually 300°–500° C. When a mixture of acrolein and acetaldehyde is used generally 50 to 80% of the mixture by weight is acrolein.

EXAMPLE 1

There was used the apparatus shown in FIG. 2. The gas washers were packed columns. There was led to the first washer 11 a steady stream of reaction gases 10 which were produced by separately feeding into a fluidized bed reactor in homogeneous flow per hour (1) a mixture of 2700 grams of acrolein vapor and 160 normal liters of nitrogen and (2) a mixture of 750 normal liters of ammonia and 2600 normal liters of residual gas 26 which contained 55.8 volume percent of nitrogen and 40.4 volume percent of ammonia. The reaction was carried out at a temperature of about 460° C. employing a catalyst made according to Example 1 of German OS No. 2,239,801 (and related Beschke U.S. Pat. No. 3,917,542) from aluminum oxide, magnesium nitrate and ammonium hydrogen fluoride.

The gases 10 were cooled to 50° C. in the first gas washer 11. There were added per hour to the washer 160 liters of cycling condensate 14 which was cooled in the heat exchanger 15° to 40° C. There were drawn off per hour from the cycling condensate 2920 grams of condensate 13 and this was led to working up 31. The remaining gases were further cooled to 25° C. in the second gas washer 21. There were also added per hour to the washer 21 160 liters of cycling condensate 24 which had been cooled to 20° C. in heat exchanger 25. There were drawn off from the cycling condensate per hour 1085 grams of condensate and this was led into cycling of the first washer 11. From the residual gas 26 there were burned hourly 300 normal liters as waste gas. The remaining residual gas was returned into the reactor after separation of the liquid mist dragged along.

The condensate 13 led from the first gas washer 11 consisted of 2 phases. There were added per hour 1400 ml of benzene and the phases separated. The aqueous phase was extracted with 1400 ml of benzene per hour in a countercurrent extraction column. It then contained only traces of pyridine and 3-methylpyridine and was discarded. The benzene phases were combined and fractionally distilled. The forerun which had a boiling temperature of 80° C. contained the total amount of benzene and water and was as good as free of pyridine and 3-methylpyridine. The benzene was used again for extraction. From the further fractions there were obtained per hour at a boiling temperature of 115° C. 419 grams of pyridine and at a boiling temperature of 143° C. 1037 grams of 3-methylpyridine corresponding to a yield of 98.4% of pyridine and 99.5% yield of 3-methylpyridine based on the content of reaction gases 10 supplied to pyridine and 3-methylpyridine.

EXAMPLE 2

The procedure was the same as in Example 1 except there were added reaction gases 10 which were produced by separately supplying to the reactor per hour (1) a mixture of 2320 grams of acrolein vapor, 1094 grams of acetaldehyde vapor and 200 normal liters of nitrogen and (2) a mixture of 950 normal liters of ammonia and 3300 normal liters of residual gas 26 which contained 33.5 volume percent of nitrogen and 41.0 volume percent of ammonia and then reacting the mixture of (1) and (2).

The gases 10 were cooled to 55° C. in the first gas washer 11. Per hour there were also added to the washer 11 180 liters of cycling condensate 14. Per hour there were drawn off 3630 grams of condensate 13 from the cycling condensate and led to working up 31. The remaining gases 20 were further cooled in the second gas washer 21 to 22° C. There were also added to the washer hourly 180 liters of cycling condensate 24. There were drawn off from the condensate cycle per hour 2080 grams of condensate and led into the cycle of the first washer 11. Per hour 380 normal liters of the residual gas 26 were burned as waste gas.

The condensate 13 led to the working up after addition of 1800 ml of benzene per hour separated into 2 phases. The aqueous phase was extracted with 1800 ml of benzene hourly. In the distillation of the benzene phases there resulted per hour 851 grams of pyridine and 862 grams of 3-methylpyridine corresponding to a yield of 98.4% of pyridine and 99.5% yield of 3-methylpyridine based on the content of reaction gases supplied.

The process of the invention can comprise, consist essentially of or consist of the steps set forth.

What is claimed is:

1. In a process for recovering pyridine and 3-methylpyridine prepared by the catalytic reaction of acrolein or a mixture of acetaldehyde and acrolein with ammonia at a temperature of at least 300° C. and then cooling the gas mixture formed and working up the condensate separated in the cooling the improvement comprising in a first step cooling the gaseous mixture from at least 300° C. to a temperature between 40° and 80° C. and then in a second cooling step cooling to a temperature of from 10° C. to below 40° C.

2. The process according to claim 1 wherein the condensate separated in the cooling of the gases is employed as a cooling liquid for the gases.

3. The process according to claim 2 wherein the condensate separating in the second cooling step is employed as the cooling liquid in the first cooling step.

4. The process of claim 1 wherein the first cooling step is to a temperature of 50° to 80° C.

5. The process of claim 1 wherein the cooling in the second step is to a temperature at least 20° C. below the temperature of cooling in the first cooling step.

6. In a process for recovering pyridine and 3-methylpyridine prepared by the catalytic reaction of acrolein or a mixture of acetaldehyde and acrolein with ammonia at a temperature of at least 300° C. and then cooling the gas mixture formed and working up the condensate separated in the cooling, the catalyst either (A) consisting essentially of oxygen containing compounds of Al, F, at least one of the elements B and Si and at least one element from the second and fourth groups of the periodic system selected from the group consisting of Mg, Ba, Zn, Sn and Zr, said catalyst having been prepared by heating in the presence of oxygen at a temperature of 600° to 800° C.:

1. aluminum, aluminum oxide or an aluminum compound convertible to the oxide at said temperature,
2. a compound of fluorine, said fluorine having been added as ammonium fluoride, ammonium hydrogen fluoride, hydrogen fluoride, fluoboric acid, fluosilicic acid, boron trifluoride, magnesium fluoborate, magnesium fluosilicate, zinc fluosilicate or barium fluosilicate,
3. boron, silicon, boric oxide, silica or a compound of boron or silica convertible to the oxide at said temperature and
4. magnesium, zinc, tin, zirconium, magnesium oxide, zinc oxide, tin oxide or a compound of zirconium or barium convertible to the oxide at said temperature, the atomic ratio of Al to F being from 1000:25 to 1000:800 and the atomic ratio of Al fo the total of (3) and (4) being from 1000:5 to 100:200, the atomic ratio of the total of boron and silicon to the other element from the second and fourth groups being between 1 to 10 and 10 to 1, or (B) having been prepared by heating at 600° to 800° C. in the presence of gaseous oxygen, (1) aluminum metal, aluminum oxide or a compound of aluminum convertible to the oxide upon heating with gaseous oxygen at 600° to 800° C., (2) ammonium fluoride, hydrogen fluoride or a fluoride of an element of the second main group of the periodic system and (3) at least one element of the second main group of the periodic system, the oxide of said element or a compound of said element convertible to the oxide in the presence of gaseous oxygen at a temperature of 600° to 800° C., said catalyst consisting essentially of the elements Al, F, O and the element of the second main group of the periodic system, or (C) consisting essentially of the product obtained by treating with oxygen at a temperature of 550° to 1200° C. compounds of the elements Al, F and O and at least two other elements selected from the second, fourth, fifth and sixth groups of the periodic system, said two other elements being selected from the group consisting of Mg, Ba, Zr, Sn, Ti, P, Ta, Sb and S, the ratios of the elements being Al to F of between 1000 to 10 and 1000 to 800 and of Al to the elements of the second, fourth, fifth and sixth groups being between 1000 to 5 and 1000 to 2000, the improvement comprising in a first step cooling the gaseous mixture from at least 300° C. to a temperature between 40° and 80° C. and then in a second cooling step cooling to a temperature of from 10° C. to below 40° C. and thereby separating the pyridine and 3-methylpyridine from the ammonia.

7. The process according to claim 6 wherein the condensate separated in the cooling of the gases is employed as a cooling liquid for the gases.

8. The process according to claim 7 wherein the condensate separating in the second cooling step is employed as the cooling liquid in the first cooling step.

9. The process of claim 7 wherein the first cooling step is to a temperature of 50° to 80° C.

10. The process of claim 6 wherein the cooling in the second step is to a temperature at least 25° C. below the temperature of cooling in the first cooling step.

* * * * *